US012806150B2

(12) United States Patent
Gupta et al.

(10) Patent No.: US 12,806,150 B2
(45) Date of Patent: Nov. 24, 2026

(54) EXOSOME-MEDIATED TRANSFECTION FOR DELIVERY OF NUCLEIC ACIDS

(71) Applicants: 3P Biotechnologies, Inc., Louisville, KY (US); University of Louisville Research Foundation, Louisville, KY (US)

(72) Inventors: Ramesh C. Gupta, Prospect, KY (US); Radha Munagala, Cary, NC (US); Jeyaprakash Jeyabalan, Louisville, KY (US); Rena Margaret Wallen, Clarksville, IN (US); Wendy A. Spencer, Lexington, KY (US); Farrukh Aqil, Louisville, KY (US)

(73) Assignees: University of Louisville Research Foundation, Louisville, KY (US); 3P Biotechnologies, Inc., Prospect, KY (US)

( * ) Notice: Subject to any disclaimer, the term of this patent is extended or adjusted under 35 U.S.C. 154(b) by 680 days.

(21) Appl. No.: 17/425,928

(22) PCT Filed: Jan. 27, 2020

(86) PCT No.: PCT/US2020/015259

§ 371 (c)(1),
(2) Date: Jul. 26, 2021

(87) PCT Pub. No.: WO2021/154205

PCT Pub. Date: Aug. 5, 2021

(65) Prior Publication Data

US 2022/0347109 A1 Nov. 3, 2022

(51) Int. Cl.

| | |
|---|---|
| ***A61K 9/50*** | (2006.01) |
| ***A61K 35/20*** | (2006.01) |
| ***A61P 35/00*** | (2006.01) |
| ***C12N 15/113*** | (2010.01) |
| ***C12N 15/88*** | (2006.01) |

(52) U.S. Cl.

CPC ............ *A61K 9/5068* (2013.01); *A61K 35/20* (2013.01); *A61P 35/00* (2018.01); *C12N 15/113* (2013.01); *C12N 15/88* (2013.01); *C12N 2310/14* (2013.01); *C12N 2320/32* (2013.01)

(58) Field of Classification Search

CPC ....... A61K 9/5068; A61K 35/20; A61P 35/00; C12N 15/113; C12N 15/88; C12N 2310/14; C12N 2320/32

See application file for complete search history.

(56) References Cited

U.S. PATENT DOCUMENTS

| | | | | |
|---|---|---|---|---|
| 9,943,482 | B2 * | 4/2018 | Gupta | A61K 31/7042 |
| 10,329,561 | B2 | 6/2019 | Seow et al. | |
| 10,420,723 | B2 * | 9/2019 | Gupta | A61K 9/0043 |
| 2017/0253888 | A1 | 9/2017 | Gebeyehu et al. | |
| 2018/0193270 | A1 * | 7/2018 | Bolen | A61K 47/554 |
| 2020/0392473 | A1 | 12/2020 | Zhang et al. | |
| 2021/0052496 | A1 | 2/2021 | Hart et al. | |
| 2021/0214217 | A1 | 7/2021 | Lodish et al. | |
| 2021/0238248 | A1 | 8/2021 | Llorente et al. | |
| 2022/0287967 | A1 | 9/2022 | Jyothi et al. | |

FOREIGN PATENT DOCUMENTS

| | | | | |
|---|---|---|---|---|
| WO | 2014054588 | A1 | 4/2014 | |
| WO | 2017151733 | A1 | 9/2017 | |
| WO | 2018102397 | A9 | 6/2018 | |
| WO | WO-2018102397 | A1 * | 6/2018 | A61K 31/713 |
| WO | 2020223642 | A1 | 11/2020 | |

OTHER PUBLICATIONS

Fu, Y. et al. "Recent progress in microRNA-based delivery systems for the treatment of human disease". ExRNA, vol. 1(2019), p. 24 (1-14) (Year: 2019).*

Domínguez-Arca, V. et al. "Liposomes embedded in layer by layer constructs as simplistic extracellular vesicles transfer model". Materials Science & Engineering, vol. C121 (2021), P. 111813. (Year: 2021).*

Millán Cotto, H.A. et al. "Cationic-motif-modified exosomes for mNA delivery to retinal photoreceptors". Journal of Materials Chemistry B, vol. 12 (2024), pp. 7384-7400. (Year: 2024).*

Munagala et al., Bovine milk-derived exosomes for drug delivery, Cancer Lett 2016, v 371, pp. 48-61.

Munagala, Radha, et al., Exosome-Mediated Delivery of RNA and DNA for Gene Therapy, Cancer Lett. May 1, 2021, 505: 58-72.

* cited by examiner

*Primary Examiner* — Nancy J Leith
*Assistant Examiner* — ALexandra Geraldine Dace Denito
(74) *Attorney, Agent, or Firm* — Law Office of J. L. Simunic; Joan L. Simunic

(57) ABSTRACT

The present development is a transfection reagent prepared by ionic interaction of colostrum powder-derived exosomes and a polycation. The resulting exosome-polycation matrix, or EPM, is entrapped with biologic materials, such as siRNA, mRNA, antisense oligo or plasmid DNA or a plasmid DNA expression construct.

14 Claims, 10 Drawing Sheets

EXOSOME-MEDIATED TRANSFECTION FOR DELIVERY OF NUCLEIC ACIDS

CROSS-REFERENCE TO PRIOR APPLICATIONS

The present application claims priority to PCT application PCT/US20/15259, filed 27 Jan. 2020, which is incorporated herein by reference in its entirety.

FIELD OF THE INVENTION

The invention relates to an exosome-mediated transfection reagent for delivery of RNA and DNA.

BACKGROUND OF THE INVENTION

Targeted delivery of nucleic acids to various cells has a wide range of applications, including gene therapy to treat disease, disease prevention, diagnostics, anti-aging and overall health benefits which can have a substantial economic impact on major industries such as the pharmaceutical, cosmeceutical and food and nutraceutical industries.

Transfection, the transient introduction of exogenous nucleic acids into eukaryotic cells, can accommodate different types of nucleic acids including naked DNA, plasmid DNA, CRISPR, small interfering RNA (siRNA), micro RNA (miRNA), mRNA, antisense oligonucleotides (ASO) and aptamers. An inherent problem with transfection is the gastro-intestinal (GI) uptake and rapid degradation of the unprotected nucleic acids. Generally classified into two categories, viral and non-viral transfection methods have been developed to minimize this challenge. However, lack of efficient and safe gene carriers continue to limit the development of gene therapy to a clinical level.

Viral-mediated transfection, as the name implies, uses replication-deficient viral particles from viruses such as retrovirus, lentivirus, adenovirus and herpes simplex virus to deliver the genetic material. While viral carriers may achieve a high delivery efficiency, serious risks of immunostimulation and immune rejection hinder its clinical translation, and only very small pieces of DNA can by transfected. Difficulties in production of the modified vector, increased risk of random insertion sites, and cytopathic, cytotoxic, carcinogenic and mutagenic effects have further limited acceptance of viral carriers.

Non-viral carriers (polymers, lipids and liposomes, peptides, synthetic nanocarriers) for gene delivery have advantages over their viral counter parts in that they are generally nonimmunogenic and often have designed functions to deliver larger genetic payloads with a greater potential for large-scale production. Clinical development of these non-viral vectors has been hindered, however, due to accumulation of polymer-nucleic acid complexes in specific tissues such as the liver, spleen and kidney, and their lower delivery efficiency compared to viral vectors as these synthetic carriers are unable to effectively transport their payloads to their target within the cell. For example, aggregation in physiological fluids of some types of nanoparticle carriers that are positively charged has been observed in the blood resulting from colloidal instability or interaction of the nanoparticles with blood components such as serum proteins and erythrocytes resulting in rapid clearance by circulating macrophages thus preventing local delivery. Liposomal delivery of DNA was introduced in 1980 and has advanced the most in drug delivery. However, liposome formulations suffer from short blood-circulation time, instability in vivo, and a lack of target selectivity. Targeted liposomal formulations using immunoliposomes have shown improved efficacy; however, the immunoliposomes are rapidly eliminated from cells. Polymer-based delivery systems offer the advantages of linking various ligands to the surface; however, their use is restricted due to high costs, scalability and toxicity issues.

Natural nanoparticles, such as exosomes, offer an improvement to both viral and synthetic carriers as nucleic acid delivery vectors. These lipid-bilayer nanovesicles (30-100 nm), whose endogenous function is to facilitate inter-cellular communication, are secreted by all cell types and occur naturally in all bodily fluids, including breast milk, and can overcome the limitations of many other delivery approaches. In particular, exosomes have the potential to provide an appropriate delivery system due to their nano size, the capability of loading a variety of agents including small drug molecules and macromolecules and including DNA and RNA, the capacity to stabilize and protect their payload from degradation, the ability to cross the blood brain barrier, the lack of toxicity and immunogenicity, and the capacity for modification of membrane proteins to further increase targeted-delivery. One of the major limitations of exosomes as nucleic acid delivery vectors is the ability to load an effective amount of the DNA/RNA. While electroporation and Exo-Fect™ have been shown to somewhat improve loading efficiency compared with standard incubation methods, their use has been restricted to mostly cell culture and limited pre-clinical models due to scale-up and toxicity issues.

Polycations, such as polyethylenimine (PEI), are among the most studied polymers for genetic transfection. PEI as a gene transfectant was first demonstrated in vitro and in vivo in 1995. A major limitation of PEI as a transfecting agent for clinical translation, however, is its substantial cytotoxicity, which can be mitigated by a range of chemical modifications, but which may suppress the transfection efficiency. The highly cationic nature of PEI also prevents its application for oral delivery.

Thus, it would be beneficial to have a transfection reagent for the delivery of nucleic acids which was efficient, effective, presented nominal toxicity risks, and could be applicable for oral delivery.

SUMMARY OF THE PRESENT INVENTION

The present development is a transfection reagent comprising an isolated exosome complexed with a polycation, and further embedded with a biological material. The exosome-polycation matrix-nucleic acid complex is effective for transfecting cells with nucleic acid to knockdown target gene expression, to introduce gene expression, to enhance gene expression, or to increase immune recognition of disease cells. In one exemplary embodiment, the exosome is isolated from bovine colostrum. In a first alternative exemplary embodiment, the polycation is polyethylenimine. In a second alternative exemplary embodiment, the biologic materials are selected from siRNA or plasmid DNA.

The present development is also a method for preparation of the transfection reagent. The transfection reagent is prepared by initially preparing an exosome-polycation matrix, or EPM, and then entrapping a nucleic acid with the EPM. The EPM is prepared by ionic interaction of the exosomes and the polycation. The biologic materials are entrapped in the EPM with a high loading by electrostatic interaction.

The present development is also a method for using the transfection reagent to knockdown target gene expression, to introduce gene expression, to enhance gene expression, or to increase immune recognition of disease cells. Cells are transfected with the EPM-nucleic acid complex to deliver the biologic while maintaining the integrity of the biologic material.

DETAILED DESCRIPTION OF THE PRESENT DEVELOPMENT

Figure 1:
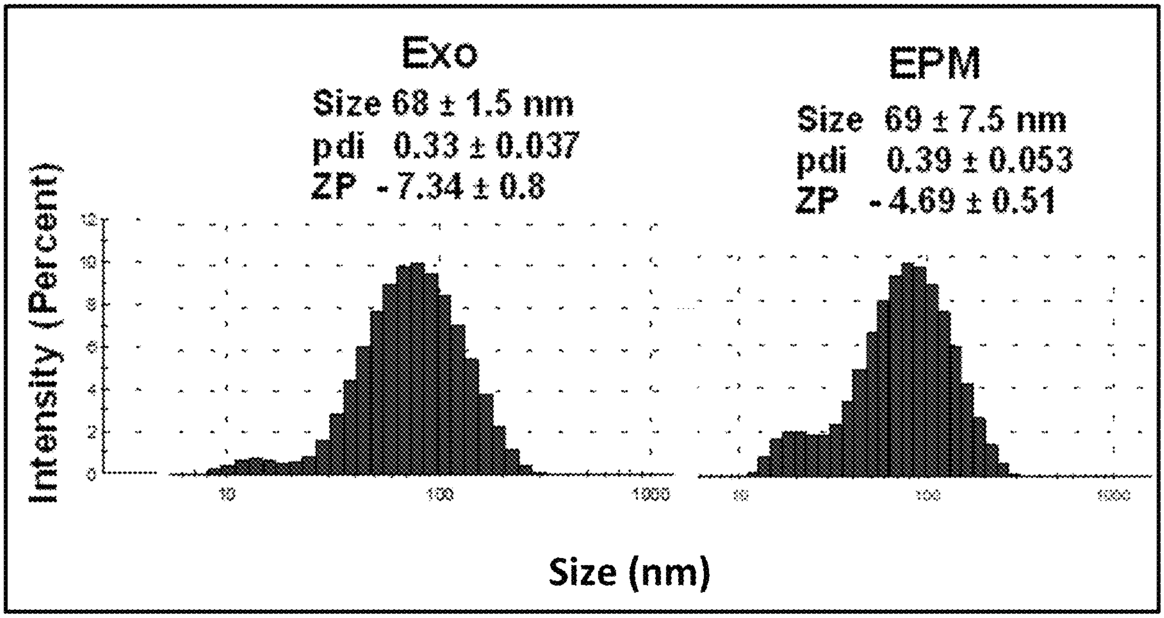
FIG. 1 is a pair of graphs showing the size, polydispersity distribution (pdi), and zeta potential (ZP) of isolated bovine colostrum powder-derived exosomes, labeled "Exo", and of isolated bovine colostrum powder-derived exosomes complexed with polyethylenimine, labeled "EPM", as measured by Zetasizer®.

The present development is an exosome-polycation matrix, or EPM, embedded with nucleic acid to produce an EPM-nucleic acid complex. In a preferred embodiment, the EPM comprises exosomes isolated from bovine colostrum powder and the polycation is polyethylenimine, and the nucleic acid embedded on the EPM is selected from an siRNA or a plasmid DNA or a plasmid DNA expression construct or a combination thereof.

The EPM-nucleic acid complex is effective for the delivery of nucleic acids through transfection. More specifically, the EPM-nucleic acid complex is effective for transfecting cells with nucleic acid to knockdown target gene expression, to introduce gene expression, to enhance gene expression, or to increase immune recognition of disease cells. Exemplary cells for transfection are lung cancer cells, breast cancer cells, pancreatic cancer cells, cervical cancer cells, ovarian cancer cells, colon cancer cells, liver cancer cells, bladder cancer cells, renal cancer cells, brain cancer cells, thyroid cancer cells, brain cells, kidney cells, liver cells, spleen cells, lymph node cells, lung cells, pancreatic cells, and combinations thereof. In preferred embodiments, transfection of lung cancer cells is with eGFP plasmid DNA or siRNA, and transfection of lung cancer cells null in p53 is with p53 plasmid DNA. It has also been found that significant silencing by different siRNAs in multiple human cancer cell lines is observed by loading isolated exosomes with siRNA using a chemical transfecting reagent.

The following description is intended to provide the reader with a better understanding of the invention. The description is not intended to be limiting with respect to any element not otherwise limited within the claims. For example, the present invention will be described in the context of use with exosomes isolated from bovine milk and from bovine colostrum, but the teachings herein are not limited to bovine milk or bovine colostrum. Representative examples of EPM-nucleic acid complexes that may be prepared according to the present development, methods for preparation, and uses of the EPM-nucleic acid complexes prepared will also be provided here. These examples are intended to provide the reader with a better understanding of the invention, but it is to be understood that these examples are not intended to be all-inclusive or limiting in any respect as related to the present invention or intended claims.

The exosome-polycation matrix is prepared by complexation or by ionic interaction of isolated exosomes and a polycation. The exosomes may be isolated from a variety of sources known in the art. For the uses described herein, a preferred embodiment uses exosomes derived from milk or colostrum, in raw liquid form or as a powder, and a more preferred embodiment uses exosomes derived from bovine milk or bovine colostrum powder. However, other milk or colostrum sources may be used. The polycation may be any polycation known in the art for transfection or that can serve as a vehicle for delivery of nucleic acids, such as but not limited to polyethylenimine, polyethylenimine conjugates, polycationic peptides, polylysine, polyornithine, polyhistidine, polyarginine, DEAE-dextran, chitosan, polyamine dendrimers, cationic lipids, cationic phospholipids, and combinations thereof. In a preferred embodiment, the polycation is polyethylenimine.

A recommended method for preparation of the EPM is by isolating exosomes from bovine colostrum powder and then incubating the exosomes with the polycation to form the EPM. In a preferred embodiment, the EPM is prepared by ionic interaction of exosomes isolated from bovine colostrum powder and polyethylenimine. The polyethylenimines used for the examples reported herein are selected from the group consisting of PEI 60,000 MW (PEI-60K), PEI branched chain MW 800, PEI linear chain MW 2,500, and PEI-g-polyethylene glycol (PEI-PEG), although it is anticipated that other polyethylenimines may be used. It has been found by the inventors that for treatment of lung cancer cell lines, a PEI having a molecular weight of at least 5,000 is the more effective than lower molecular weight polyethylenimines and that PEI-60K had the greatest gene knocking in the studies the inventors have completed.

As is known in the art, exosomes may be isolated using a variety of means. In a recommended embodiment, exosomes are isolated from bovine colostrum powder by obtaining a sample of bovine colostrum powder and rehydrating the powder in phosphate-buffer-saline (PBS, pH 7.4), and then isolating the exosomes by differential centrifugation following the conditions described in Munagala et al. Cancer Letts. 371:48-61, 2016. The isolated exosomes are incubated with varying concentrations of PEI (0.015%-0.4%) and the resulting complex is isolated by precipitation with ExoQuick® or PEG-400 or by molecular weight cutoff spin filtration or ultracentrifugation. The precipitate is suspended in phosphate-buffered-saline (PBS), pH 7.4. Size and polydispersity dispersion index (pdi) of the EPM, as well as exosomes and free PEI are measured by dynamic light scattering (DLS) or Zetasizer®. In one representative preparation, data showed that both exosomes and PEI were below 100 nm in size. As shown in FIG. 1, the size of the complexed exosome or EPM is essentially the same as that of the uncomplexed exosomes and the pdi value of the EPM is essentially the same as the pdi of the uncomplexed exosome, but the zeta potential is somewhat increased.

Figure 2:
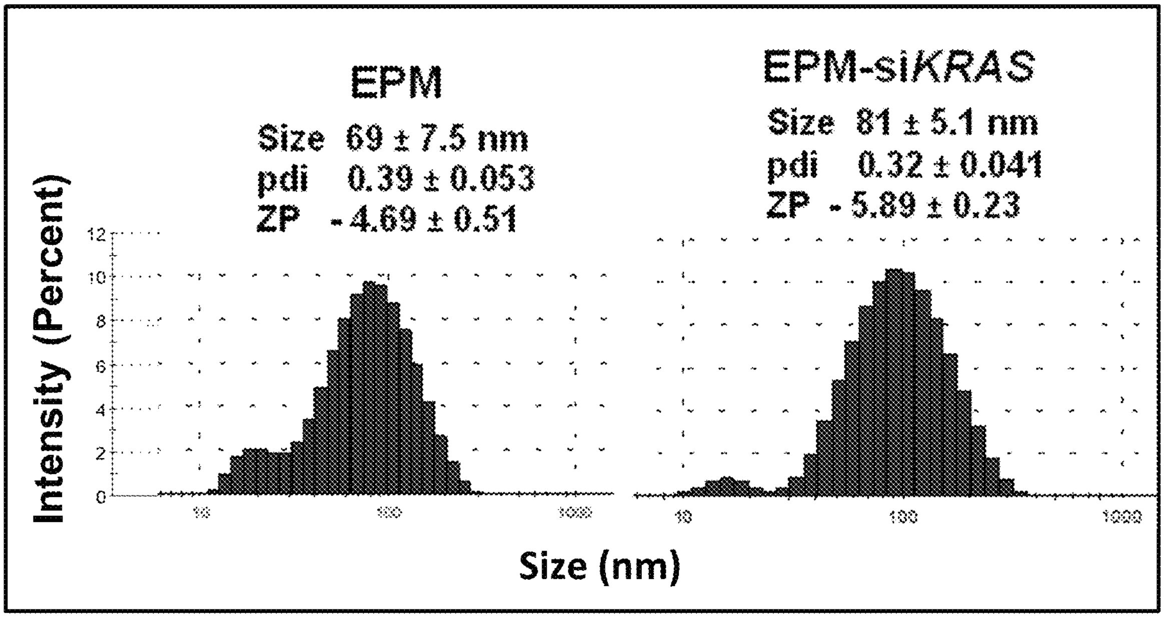
FIG. 2 is a pair of graphs showing the size, polydispersity distribution (pdi), and zeta potential (ZP) of isolated bovine colostrum powder-derived exosomes complexed with polyethylenimine, labeled "EPM", and of the EPM embedded with siKRAS, labeled "EPM-siKRAS", as measured by Zetasizer®.

The EPM-nucleic acid complex is prepared by incubating the EPM with a nucleic acid, and then harvesting EPM-nucleic acid complex. In a first embodiment, the nucleic acid is an siRNA, such as, siEGFR, SiKRAS, siAKT, siMAPK, siVEGF, or a combination thereof. In a first alternative embodiment, the nucleic acid is a plasmid DNA, such as eGFP, p53, mRNA, an antisense oligo (ASO), an aptamer, or a combination thereof. As shown in FIG. 2, the size of the EPM-nucleic acid complex is slightly larger than the size of the EPM, the pdi value of the EPM-nucleic acid complex is essentially the same as the pdi of the EPM, and the zeta potential is somewhat reduced for the EPM compared to the EPM-nucleic acid complex.

As is known in the art, the exosomes may be covalently attached to a highly fluorescent dye, such as AF750 to form Exo-AF750. The Exo-AF750 may then be complexed with the polycation PEI to form AF750-tagged Exo-PEI (the EPM). Alternatively, the exosomes may be functionalized with tumor-targeting ligand folic acid (FA), and then attached with the fluorescent dye AF750, followed by complexation with PEI to form AF750-tagged FA-Exo-PEI (FA-EPM).

For comparison to the EPM-nucleic acid complex of the present invention, exosome-nucleic acid compositions can be prepared by incubating isolated exosomes with a nucleic acid in the presence of a chemical transfecting agent, such as Exo-Fect™. For example, an isolated exosome may be incubated with Exo-Fect™ and siRNA to produce Exo-siRNA. When Exo-Fect™ is used, the polycation is not included in the composition.

In order to more easily study the EPM-nucleic acid complexes formed, the siRNA—specifically, siVEGF (VEGF=vascular endothelial growth factor) and siKRAS (KRAS=kirsten rat sarcoma virus)—can be labeled with $5'\text{-}^{32}P$ by T4 polynucleotide kinase-catalyzed phopsphorylation in the presence of $[r\text{-}^{32}P]$ATP (>6,000 Ci/mmol). When using labeled starting materials, as is known in the art, it is recommended that the reaction conditions are adjusted such that all of the ATP is consumed in the reaction.

In examples conducted in the inventors' laboratories, the labeled siRNA was purified using a GE Healthcare ProbeQuant® G-50 Micro Column, followed by further purification using either a mirVana™ miRNA Isolation Kit (from Invitrogen) or polyacrylamide gel electrophoresis (PAGE). Analysis of the purified labeled siRNA by PAGE followed by detection by Packard InstantImager™ showed the labeled siRNA was essentially free from any radioactive contaminants. Unless otherwise indicated, $^{32}P$-labeled siVEGF or siKRAS was included in each reaction described herein as a tracer.

Preparation of an EPM-siRNA Complex:

Loading of siRNA onto the EPM. From about 25 μg to about 300 μg isolated exosomes are incubated with the specified polycation in the presence of from about 0.30 μg to about 50 μg siRNA in 150 μl PBS, pH 7.4. After incubation at about 23° C.±5° C. for up to about 60 minutes, the exosome-polycation-nucleic acid complex (EPM-siRNA) is isolated by precipitation with ExoQuick® or PEG-400. In a preferred embodiment, the brief incubation is a period of up to about 20 minutes. The precipitate and supernatant are separated by low-speed centrifugation and the collected precipitate, in the form of a pellet, is suspended in PBS. Table 1 provides examples of EPM-siRNA complexes.

Figure 3:
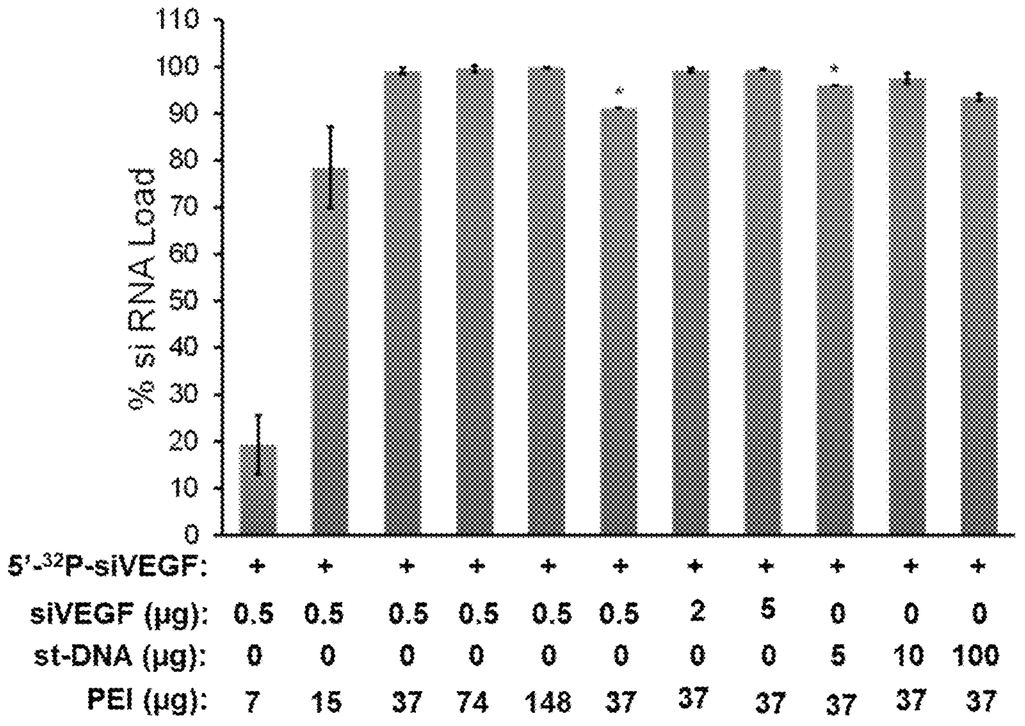
FIG. 3 is a graphical representation of the entrapment of siRNA for VEGF (siVEGF) and salmon testis DNA (stDNA) on bovine colostrum powder-derived exosomes complexed with PEI-60K, wherein the amount of siVEGF varies from 0 μg to 500 μg and the amount of stDNA varies from 0 μg to 10,000 μg.
Figure 4:
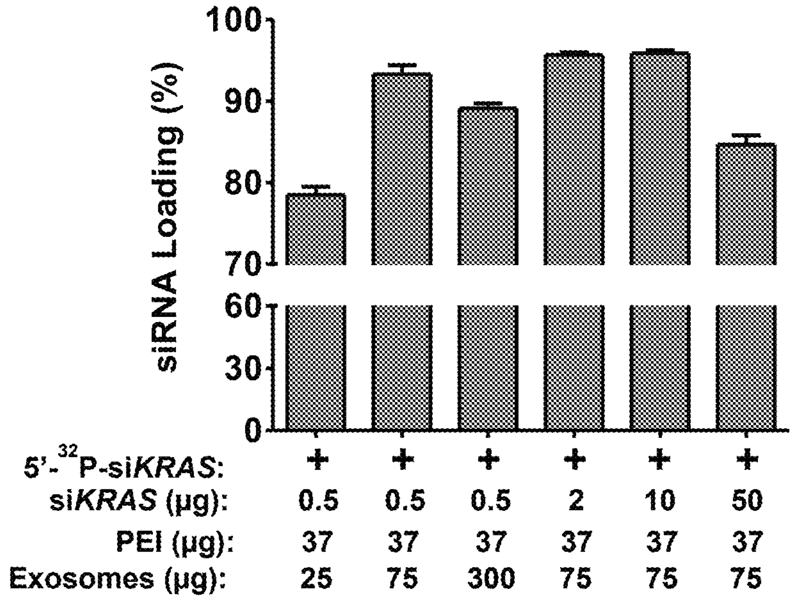
FIG. 4 is a graphical representation of the entrapment of siRNA for KRAS (siKRAS) on bovine colostrum powder-derived exosomes complexed with PEI-60K, wherein the amount of siKRAS varies from 0.5 μg to 50 μg.
Figure 5:
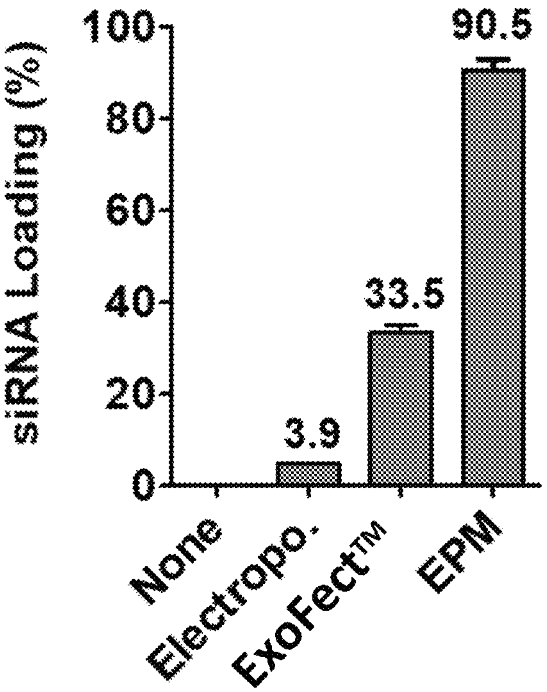
FIG. 5 is a bar graph comparing the siRNA entrapment observed by treating bovine colostrum powder-derived exosomes with siKRAS in the presence of PEI-60K ("EPM"), and by treating bovine colostrum powder-derived exosomes with siKRAS in the presence of the chemical transfecting reagent Exo-Fect™, and by treating bovine colostrum powder-derived exosomes with siKRAS using electroporation ("Electropo"), and by treating bovine colostrum powder-derived exosomes with siKRAS without any chemical or physical additives ("None")

Determination of amount of radioactive siRNA complexed to EPM. To determine the amount of the radioactive siRNA complexed with the EPM, or the siRNA loading, aliquots of the EPM pellet and of the supernatant are applied to a piece of thin layer PEI-cellulose and the radioactivity is analyzed by Packard InstantImager™. The percent radioactivity in the EPM-siRNA complex is calculated by dividing the measured radioactivity in the collected pellet by the total measured radioactivity in the collected pellet and supernatant, and multiplying the ratio by 100. FIG. 3 shows the percent entrapment of siVEGF and salmon testes DNA (stDNA) onto the EPM under various experimental conditions. FIG. 4 shows the percent entrapment of siKRAS onto the EPM under various experimental conditions.

labeled "EPM", 37 μg PEI-60K was added to the incubating mixture as described supra using an incubation temperature of about 23° C. for about 20 minutes. For each reaction, the exosomal-siRNA formation was recovered by precipitation with ExoQuick® or PEG-400 and the precipitate was suspended in PBS. Measurement of the radioactivity in the precipitated formulation and the supernatant indicated the proportion of the siRNA loaded into/onto exosomes. As shown in FIG. 5, the highest siRNA entrapment is observed with the EPM and the lowest siRNA entrapment is observed with the electroporation method.

Enzymatic degradation of siRNA loaded onto the EPM: To determine if siRNA loaded onto the EPM is protected from enzymatic degradation, the siKRAS/$^{32}$P-siKRAS loaded onto EPM was incubated with varying concentrations of RNase A using an incubation temperature of about 23° C. for about 30 minutes, the hydrolysate was purified by GE

TABLE 1

| | Exosome | | Polycation | | siRNA | | siRNA loading |
|---|---|---|---|---|---|---|---|
| Example | Source | Amt (μg) | Source | Conc (μg) | Type | Amt (μg) | % |
| 1 | bov colostrum | 300 | PEI-60K | 7.5 | siVEGF | 0.30 | 18 |
| 2 | bov colostrum | 300 | PEI-60K | 15 | siVEGF | 0.30 | 78 |
| 3 | bov colostrum | 300 | PEI-60K | 37 | siVEGF | 0.30 | >98 |
| 4 | bov colostrum | 300 | PEI-60K | 75 | siVEGF | 0.30 | >98 |
| 5 | bov colostrum | 300 | PEI-60K | 150 | siVEGF | 0.30 | >98 |
| 6 | bov colostrum | 300 | PEI-60K | 37 | siVEGF | 2.00 | >95 |
| 7 | bov colostrum | 300 | PEI-60K | 37 | siVEGF | 5.00 | 95 |
| 8 | bov colostrum | 300 | PEI-60K | 37 | stDNA[1] | 500 | 95 |
| 9 | bov colostrum | 300 | PEI-60K | 37 | stDNA[1] | 10.00 | 98 |
| 10 | bov colostrum | 300 | PEI-60K | 37 | stDNA[1] | 100.00 | 95 |
| 11 | bov colostrum | 300 | PEI-60K | 37 | siKRAS[2] | 0.50 | 90 |
| 12 | bov colostrum | 75 | PEI-60K | 37 | siKRAS[2] | 0.50 | 94 |
| 13 | bov colostrum | 75 | PEI-60K | 37 | siKRAS[2] | 2.00 | 95 |
| 14 | bov colostrum | 75 | PEI-60K | 37 | siKRAS[2] | 10.00 | 95 |
| 15 | bov colostrum | 75 | PEI-60K | 7.5 | siKRAS[2] | 50.00 | 8 |
| 16 | bov colostrum | 300 | PEI-60K | 15 | siKRAS[2] + PEG[3] | 0.30 | 91 |
| 17 | bov colostrum | 300 | PEI-800 | 37 | siKRAS[2] | 0.30 | 18 |
| 18 | bov colostrum | 300 | PEI-2,500 | 37 | siKRAS[2] | 0.30 | 67 |
| 19 | bov colostrum | 300 | br ch PEI[4] | 37 | siKRAS[2] | 0.30 | 18 |
| 20 | bov colostrum | 300 | PEI-PEG | 37 | siKRAS[2] | 0.30 | 87 |
| 21 | bov colostrum | 300 | spermine | 1110 | siKRAS[2] | 0.30 | ~2 |
| 22 | bov colostrum | 300 | spermidine | 1110 | siKRAS[2] | 0.30 | ~2 |
| 23 | bov colostrum | 300 | gelatin type A | 104 | siKRAS[2] | 0.50 | <1 |
| 24 | bov colostrum | 300 | gelatin type B | 104 | siKRAS[2] | 0.50 | <1 |
| 25 | bov colostrum | 300 | dextran | 192 | siKRAS[2] | 0.50 | <1 |
| 26 | bov colostrum | 300 | chitosan med MW | 104 | siKRAS[2] | 0.50 | <1 |
| 27 | bov colostrum | 300 | chitosan high MW | 0.0 | siKRAS[2] | 0.50 | <1 |
| 28 | bov colostrum | 300 | polylysine | 1110 | siVEGF | 0.50 | <1 |

bov = bovine
1 = $^{32}$P siVEGF included as a tracer
2 = $^{32}$P siKRAS included as a tracer
3 = EPM was recovered by precipitation with PEG-400 instead of ExoQuick ®
4 = branched chain PEI, MW 800

Figure 6:
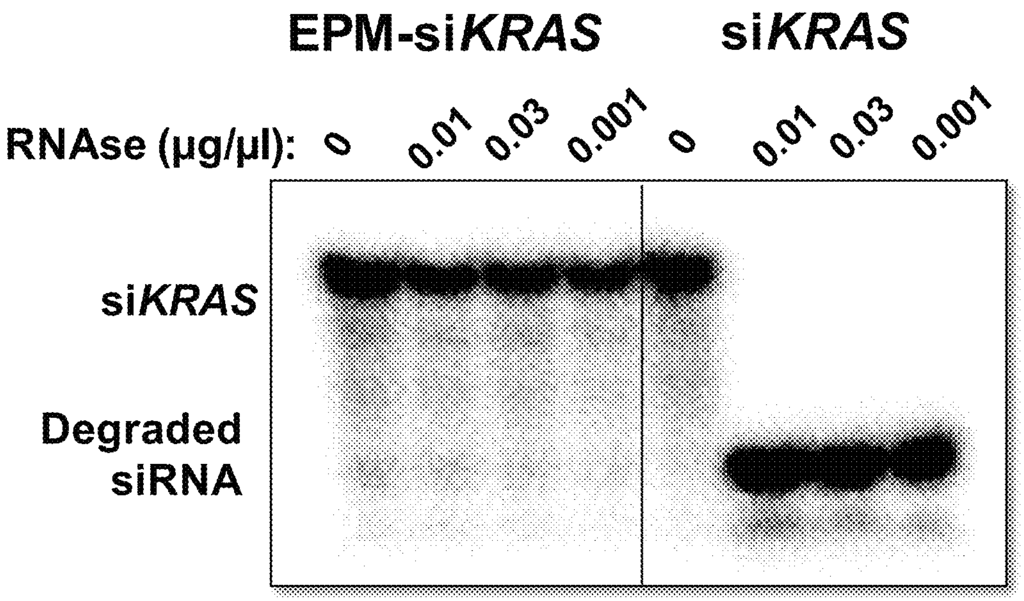
FIG. 6 is an autoradiograph of a gel electrophoresis plate comparing the stability of pure siKRAS with siKRAS loaded to the EPM when subjected to enzymatic degradation.

The amount of siRNA entrapment to exosomes was compared for three different loading methods. For each reaction, 150 μg bovine colostrum powder-derived exosomes and 10 μg of siKRAS together with $^{32}$P-labeled siKRAS were used. The efficiency in siRNA loading is shown in FIG. 5. In the baseline reaction (labelled "None"), no additional reagents or physical treatments were used and essentially no loading was detected. In an electroporation method, labeled "Electropo.", exosomes were loaded with nonradioactive and $^{32}$P-labeled siKRAS by subjecting the mixture to electroporation using Gene Pulser Xcell™. In a second method, labeled "Exo-Fect™", the exosomes were loaded with siKRAS using the chemical transfecting reagent Exo-Fect™ (available from System Biosciences) using conditions recommended by the vendor. In an EPM method, Healthcare ProbeQuant® G-50 Micro Column followed by further purification using the mirVana™ miRNA Isolation Kit, then the hydrolysate was mixed with heparin to dissociate the ionic interaction and then electrophoresed by polyacrylamide gel electrophoresis and the radioactive products were detected by Packard InstantImager™. As shown in FIG. 6, the EPM-siKRAS appears to be essentially completely protected from the enzymatic degradation under the experimental conditions whereas the naked siKRAS is completely degraded by the enzyme.

Figure 7:
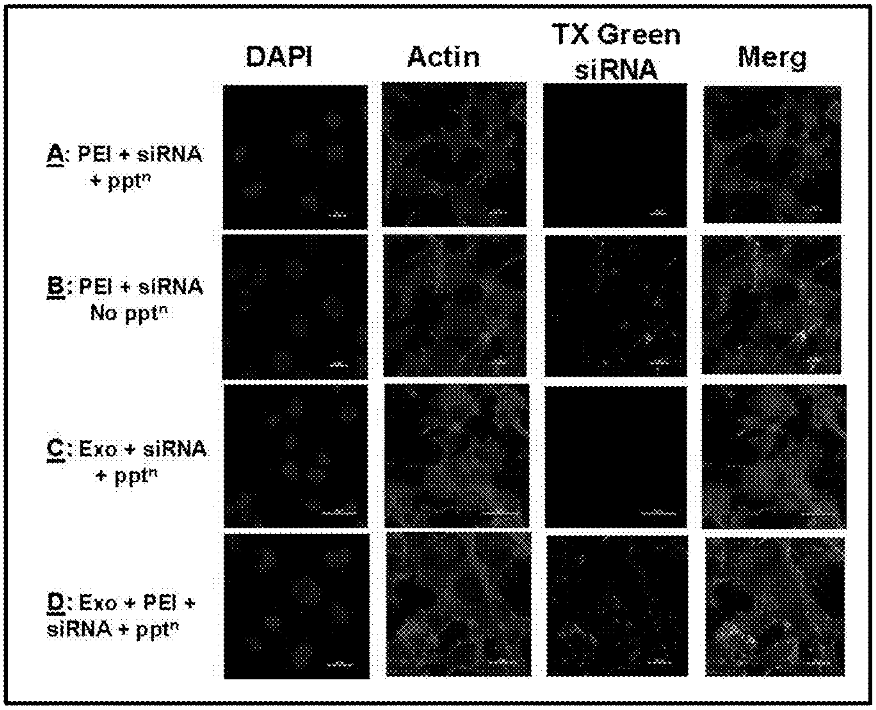
FIG. 7 is a set of micrographs of human lung cancer H1299 cells treated with Texas green siRNA loaded in bovine colostrum powder-derived exosomes complexed with PEI.
Figure 8:
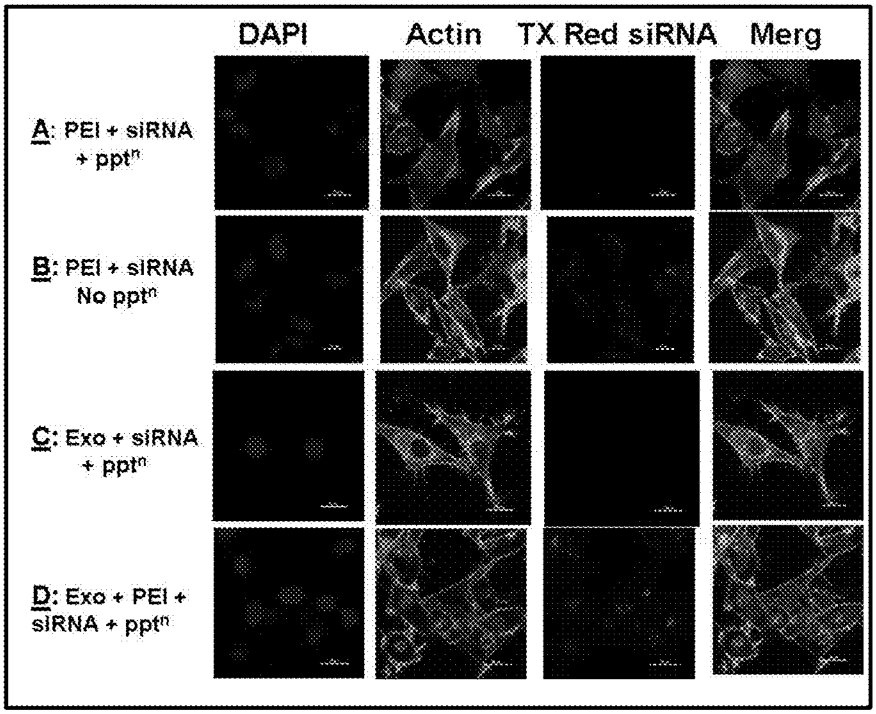
FIG. 8 is a set of micrographs of human pancreatic cancer MiPaCa2 cells treated with Texas Red® siRNA loaded in bovine colostrum powder-derived exosomes complexed with PEI.

Transfection of human cancer cells with siRNA loaded onto EPM: Human cancer cell lines (lung: H1299 and A549; breast: MDA-MB-231 and MCF-7; ovarian: OVCA; and pancreatic: Panc1, MiaPaCa2) were plated (75,000-100,000 cells per well) in a 24-well plate and treated with the EPM-siRNA, wherein the siRNA was selected from siAKT, siVEGF, siKRAS, control Texas green siRNA, control Texas Red® siRNA, and combinations thereof. Microscopic studies were performed at 24 h-48 h, while functional assay by western blot analysis were performed at 24 h-72 h treatment. Transfection using the EPM-siRNA complex was compared to siRNA loaded to exosomes using prior art methods with the chemical transfection agents Exo-Fect™ and Lipofectamine® 2000. FIGS. 7-8 are micrographs of various cancer cells treated with the siRNA loaded to the EPM. As shown in FIG. 7, when human lung cancer H1299 cells are treated with the EPM loaded with Texas green siRNA and the fixed cells are visualized under confocal microscope, cells clearly show high transfection with the siRNA with essentially no toxicity. However, the transfection is modest when cells are treated with PEI+siRNA without the precipitation step, and this formulation is accompanied with significant toxicity based on cell death. No transfection is found with PEI+siRNA, or Exo+siRNA, following the precipitation step. Similar results are obtained with human lung cancer A549 cells (data not shown). Essentially similar conclusions are made upon treatment of human pancreatic cancer MiaPaCa2 cells with EPM loaded with Texas Red® siRNA, as shown in FIG. 8, and Texas green siRNA (data not shown). When human lung cancer A549 cells are treated with EPM loaded with siKRAS and cell lysate is analyzed for the expression of the target gene by western blot, the target gene is found to be knocked down by about 80%.

Figure 9:
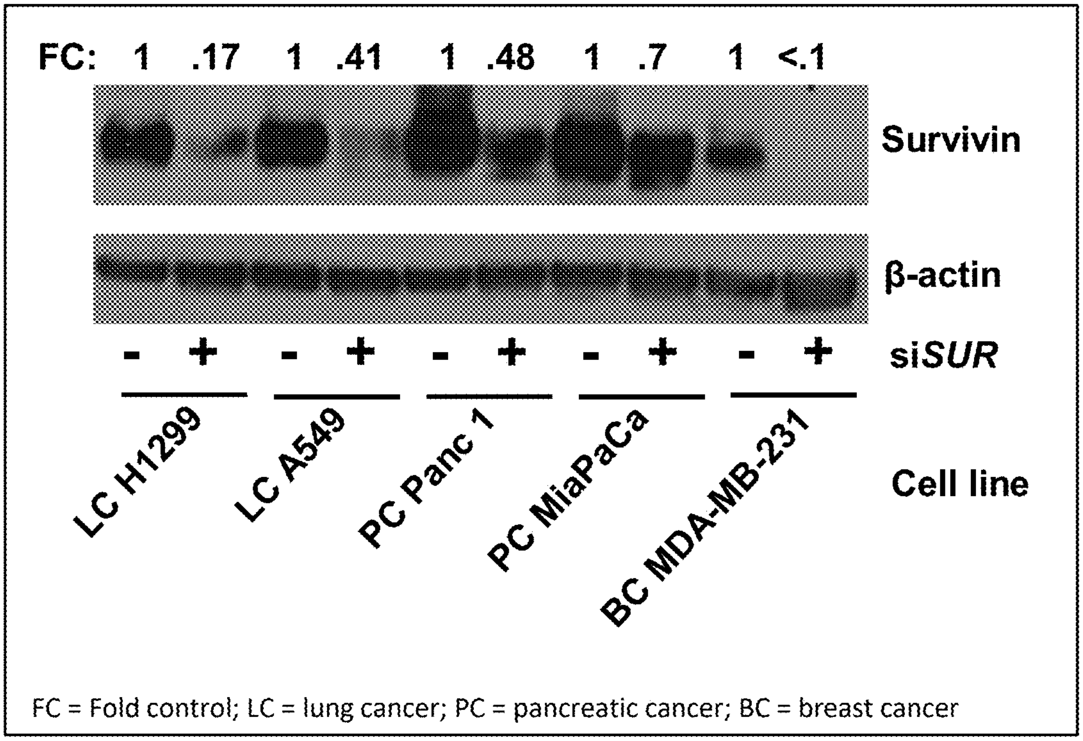
FIG. 9 is a graph showing the effect of siRNA of survivin (siSUR) loaded in bovine colostrum-derived exosomes complexed with PEI, i.e., EPM on the expression of target gene in different human cancer cell types, wherein the cell hydrolysates were analyzed by western blot analysis, and wherein β-actin served as a loading control.

In addition, as shown in FIG. 9, when human lung cancer H1299 and A549 cells are treated with EPM loaded with siSUR and the cell lysates are analyzed for the expression of the target gene by western blot, the target gene in both the cell lines are diminished by 83% and 59%, respectively. Likewise significant reductions in the target genes are also found in human pancreatic cancer Panc 1 (52%) and MiaPaCa (30%) cells, as well as in human breast cancer MDA-MB-231 cells (nearly 100%) upon treatment with EPM loaded with siSUR.

Figure 10:
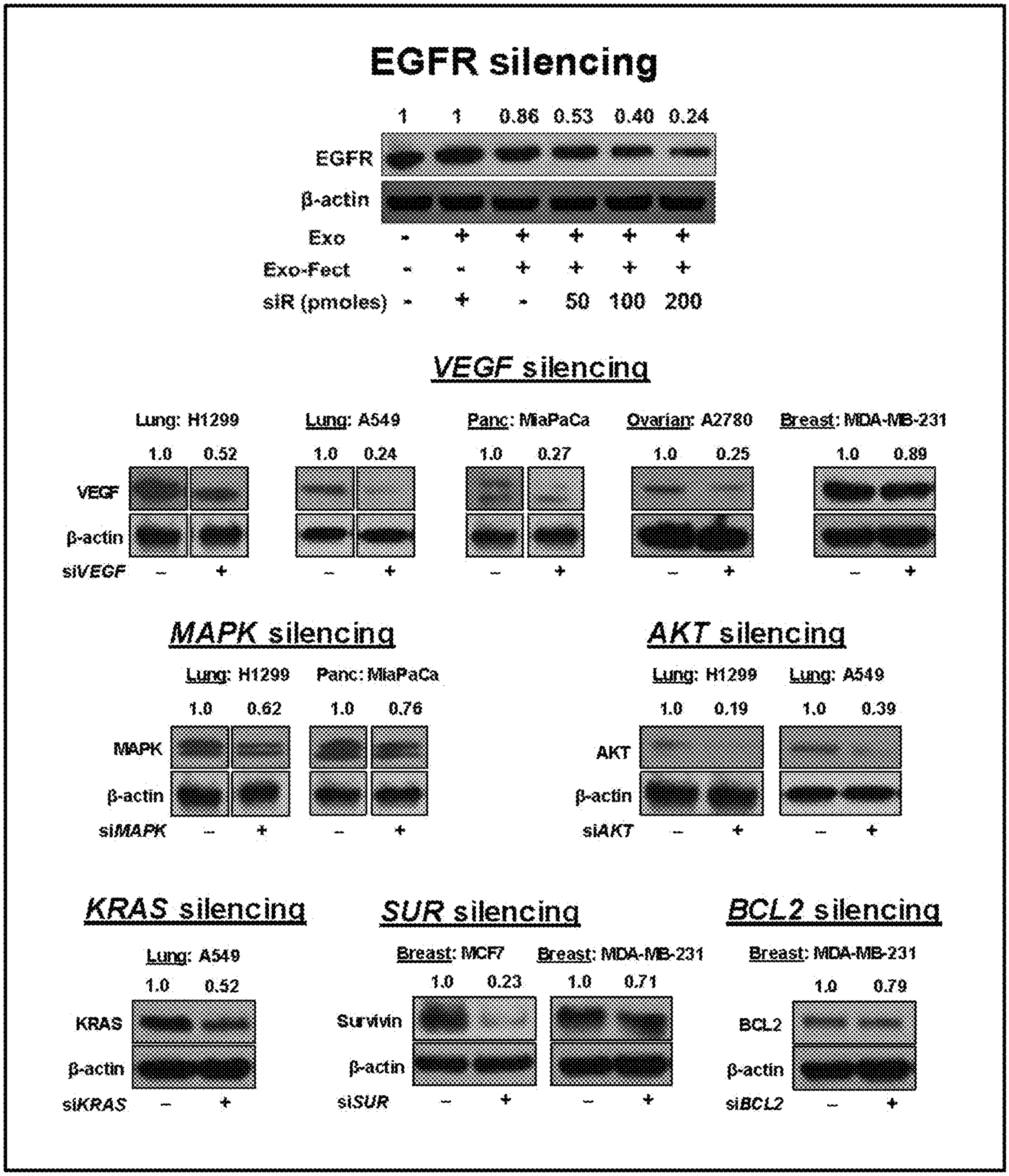
FIG. 10 is a set of western blots showing the effect specified siRNAs loaded in the exosomes by Exo-Fect™ reagent on target genes in different human cancer cell lines, followed by analysis of the cell lysate by western blot analysis.

Significant silencing by different siRNAs in multiple human cancer cell lines was also observed by loading bovine colostrum powder-derived exosomes using the chemical transfecting reagent Exo-Fect™. Exemplary cancer cell lines and siRNAs tested expression levels of the target genes compared with vehicle treatment observed are shown in FIG. 10. Table 2 provides some additional examples of silencing using Exo-Fect™.

TABLE 2

| Transfection of | with | has an expression of |
|---|---|---|
| lung cancer A549 cells | Exo-siKRAS | 48% |
| lung cancer H1299 cells | Exo-siAKT | 81% |
| lung cancer A549 cells | Exo-siAKT | 61% |
| lung cancer cells H1299 | Exo-siEGFR | 46%-76%, based on the siRNA concentration used |
| lung cancer H1299 | Exo-siVEGF | 48% |
| lung cancer A549 cells | Exo-siVEGF | 76% |
| pancreatic cancer MiaPaCa cells | Exo-siVEGF | 73% |
| ovarian cancer A2780 cells | Exo-siVEGF | 75% |
| breast cancer MDA-MB-231 cells | Exo-siVEGF | 11% |
| breast cancer MCF-7 | Exo-siSUR | 77% |
| breast cancer MDA-MB-231 | Exo-siSUR | 29% |
| lung cancer H1299 | Exo-siMAPK | 38% |
| pancreatic cancer MiaPaCa | Exo-siMAPK | 24% |
| breast cancer MDA-MB-231 | Exo-siSCl2 | 21% |

Table 3 provides some additional examples of silencing observed in lung cancer A549 cells after a treatment period of about 48 hours using EPM-nucleic acid of the present invention wherein the EPM comprises 150 μg exosomes derived from bovine colostrum powder and 37 μg PEI-60K and wherein the nucleic acid is as indicated in Table 3. As indicated in Table 3, the EPM without the nucleic acid and the nucleic acid without the EPM each demonstrate efficacy essentially equal to no treatment. However, when the EPM and nucleic acid are combined, a dose-dependent down regulation of the target gene is observed using even as little as 0.01 μg siKRAS, with an optimal effect being observed with about 2 μg siKRAS. Increasing the amount of exosome from 150 μg to 300 μg did not improve the down regulation of the target gene, and increasing the amount of exosome while increasing the amount of siKRAS actually resulted in a treatment that was significantly less efficient than the 150 μg exosome-37 μg PEI-4 μg siKRAS composition.

TABLE 3

| Exosome | | Polycation | | siRNA | | Cell lines diminished by |
|---|---|---|---|---|---|---|
| Source | Amt (μg) | Source | Amt (μg) | Type | Amt (μg) | % |
| none | 0 | none | 0 | none | 0 | 0.0 |
| none | 0 | none | 0 | siKRAS | 4 | 0.0 |
| bov colostrum | 150 | PEI-60k | 37 | none | 0 | 5.0 |
| bov colostrum | 150 | PEI-60K | 37 | siKRAS | 0.01 | 44 |
| bov colostrum | 150 | PEI-60K | 37 | siKRAS | 0.025 | 59 |
| bov colostrum | 150 | PEI-60K | 37 | siKRAS | 0.05 | 57 |
| bov colostrum | 150 | PEI-60K | 37 | siKRAS | 0.5 | 70 |
| bov colostrum | 150 | PEI-60K | 37 | siKRAS | 1 | 73 |
| bov colostrum | 150 | PEI-60K | 37 | siKRAS | 2 | 76 |
| bov colostrum | 150 | PEI-60K | 37 | siKRAS | 3 | 76 |
| bov colostrum | 150 | PEI-60K | 37 | siKRAS | 4 | 75 |
| bov colostrum | 150 | PEI-60K | 37 | siKRAS | 6 | 54 |
| bov colostrum | 150 | PEI-60K | 37 | siKRAS | 8 | 48 |
| bov colostrum | 150 | PEI-60K | 37 | siKRAS | 10 | 39 |
| bov colostrum | 75 | PEI-60K | 37 | siKRAS | 4 | 76 |
| bov colostrum | 75 | PEI-60K | 37 | siKRAS | 7 | 75 |
| bov colostrum | 75 | PEI-60K | 37 | siKRAS | 10 | 75 |
| bov colostrum | 150 | PEI-60K | 37 | siKRAS | 4 | 67 |
| bov colostrum | 150 | PEI-60K | 37 | siKRAS | 7 | 72 |
| bov colostrum | 150 | PEI-60K | 37 | siKRAS | 10 | 63 |
| bov colostrum | 300 | none | 0 | siKRAS | 4 | 26 |
| bov colostrum | 300 | PEI-60K | 37 | siKRAS | 4 | 56 |

TABLE 3-continued

| Exosome | | Polycation | | siRNA | | Cell lines diminished by |
|---|---|---|---|---|---|---|
| Source | Amt (μg) | Source | Amt (μg) | Type | Amt (μg) | % |
| bov colostrum | 300 | PEI-60K | 37 | siKRAS | 7 | 38 |
| bov colostrum | 300 | PEI-60K | 37 | siKRAS | 10 | 3.0 |

bov = bovine
$^{32}$P siKRAS included as a tracer

The length of the treatment time was also evaluated using the 150 μg exosome-37 μg PEI-4 μg siKRAS composition. As shown in Table 4, there is a time-dependence for treatment with 48 hours being the most effective.

TABLE 4

| Transfection of | with | Treatment time | Cell lines diminished by (%) |
|---|---|---|---|
| lung cancer A549 cells | Untreated | — | 0.0 |
| lung cancer A549 cells | EPM-siKRAS | 12 h | 40 |
| lung cancer A549 cells | EPM-siKRAS | 24 h | 62 |
| lung cancer A549 cells | EPM-siKRAS | 48 h | 76 |

The inventors also evaluated the effect of free polyethylene, PEI, and the effect of PEI bound to colostrum exosomes, EPM, on the cytotoxicity of A549 lung cancer cells by treating cells with varying concentrations of free PEI and EPM for 48 hours and measuring cell growth inhibition by MTT assay. A dose-dependent cytotoxicity of the free PEI was observed, but no significant cell growth inhibition was observed by treatment with EPM. These data indicate that PEI toxicity can be mitigated by embedding it in exosomes to form the EPM.

Effect of modifying the phosphate backbone on the transfection of human cancer cells with siKRAS loaded onto EPM: The effect of siKRAS with modified and unmodified phosphate backbone, embedded in the EPM on silencing of KRAS (target) protein in A549 lung cancer cells was also studied. Modifying the phosphate backbone of siKRAS is known in the art. Without limiting the scope of the invention and for the purposes of example only, the siKRAS may have a modified phosphate backbone selected from a phosphorothioate, a phosphorodithioate, a phosphoramidothioate, a phosphoramidate, a phosphordiamidate, a methylphosphonate, an alkyl phosphotriester, and a formacetal or analog thereof. Examples include, without limitation, phosphorothioate antisense oligonucleotides, such as an antisense oligonucleotide phosphothioate in the 3'-5' phosphodiester linkage to increase its stability, and chimeras between methylphosphonate and phosphodiester oligonucleotides. A549 lung cancer cells were treated for 48 h with EPM-siKRAS (modified) and EPM-siKRAS (unmodified) along with vehicle treatment and whole cell lysates were then analyzed by western blot. It was observed that the unmodified siRNA sequence is as effective as the modified sequence in silencing of the target gene.

Figure 11:
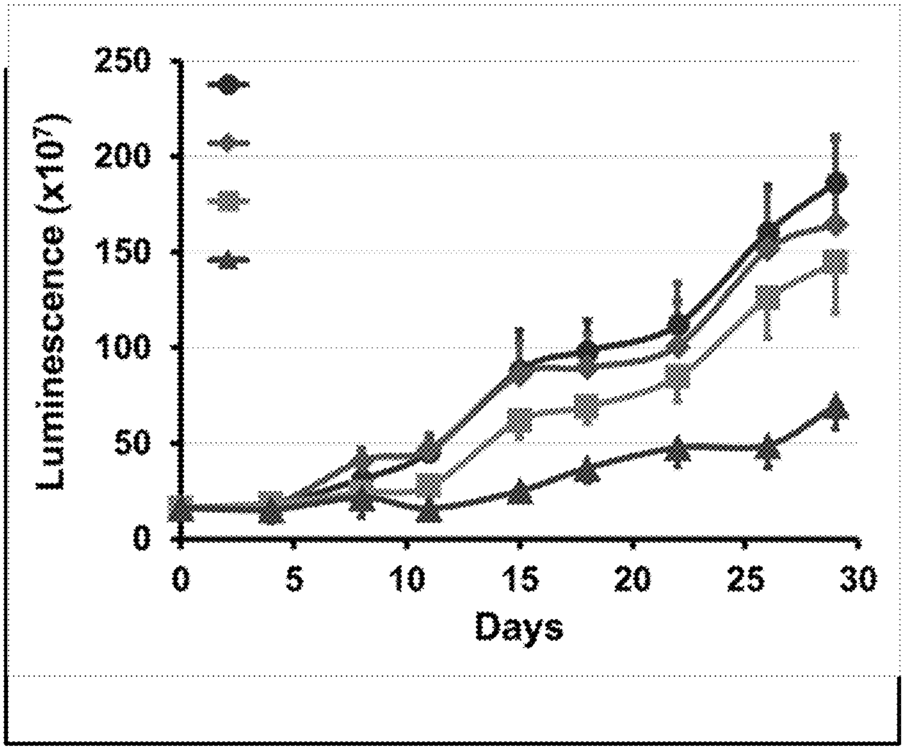
FIG. 11 is a graph showing the effect of mutated siKRAS with unmodified and modified phosphate backbone modification entrapped with folic acid (FA)-functionalized EPM on the growth of A549 lung cancer grown in tumor microenvironment in female NOD Scid mice.

Although it is standard to use siRNA in which the phosphate backbone is modified to increase stability of the siRNA, the effect of siKRAS with unmodified and modified phosphate backbone modification embedded in FA-functionalized EPM on the growth of A549 lung cancer grown in a tumor microenvironment in female NOD Scid mice was studied. Female NOD Scid mice were inoculated orthotopically with A549 lung cancer cells. When tumors grew to 80-100 mm$^3$, the animals were randomized. Separate groups of animals were treated with FA-EPM-siKRAS with a phosphate backbone modification, FA-EPM-siKRAS without a phosphate backbone modification, FA-EPM or a vehicle. The siKRAS was delivered at 20 μg siKRAS per dose in the groups receiving siKRAS. Test agents were administered intravenously three times a week. As shown in FIG. 11, a time-dependent tumor growth inhibition is observed only with the mutated siKRAS formulations. However, the inhibition is greater with the functionalized formulation and is highly significant. The FA-EPM is ineffective compared to untreated group. The tumor inhibition with FA-EPM-siKRAS is accompanied with downregulation of the target (KRAS) gene. The finding that siKRAS without any phosphate backbone modifications elicit potent anticancer effect is surprising and unexpected because published studies use siRNA sequences with modifications in order to minimize enzymatic degradability. The use of unmodified siRNAs and anti-sense oligos, or ASO, sequences can mitigate toxicity arising from the use of many types of modifications that are currently in use. Further, because the phosphate backbone modification is known to result in toxicity, having a transfection reagent that does not require phosphate backbone modification represents a significant development in the art.

The effect of siKRAS embedded in the EPM and in the standard transfection reagent Lipofectamine® on silencing of KRAS (target) protein in A549 lung cancer cells was also studied. A549 lung cancer cells were treated for 48 h with siKRAS (modified) embedded with the EPM using 75 μg exosomes or Lipofectamine® along with vehicle treatment and whole cell lysates were then analyzed by western blot. Data show the EPM-mediated transfection has greater than 70% gene knocking, which is significantly more effective than Lipofectamine®, which is the conventional transfecting reagent and has about 25% gene knocking. Increasing the siRNA amount from about 4 μg to about 7 ug or to about 10 μg does not further increase the gene knocking.

Figure 12:
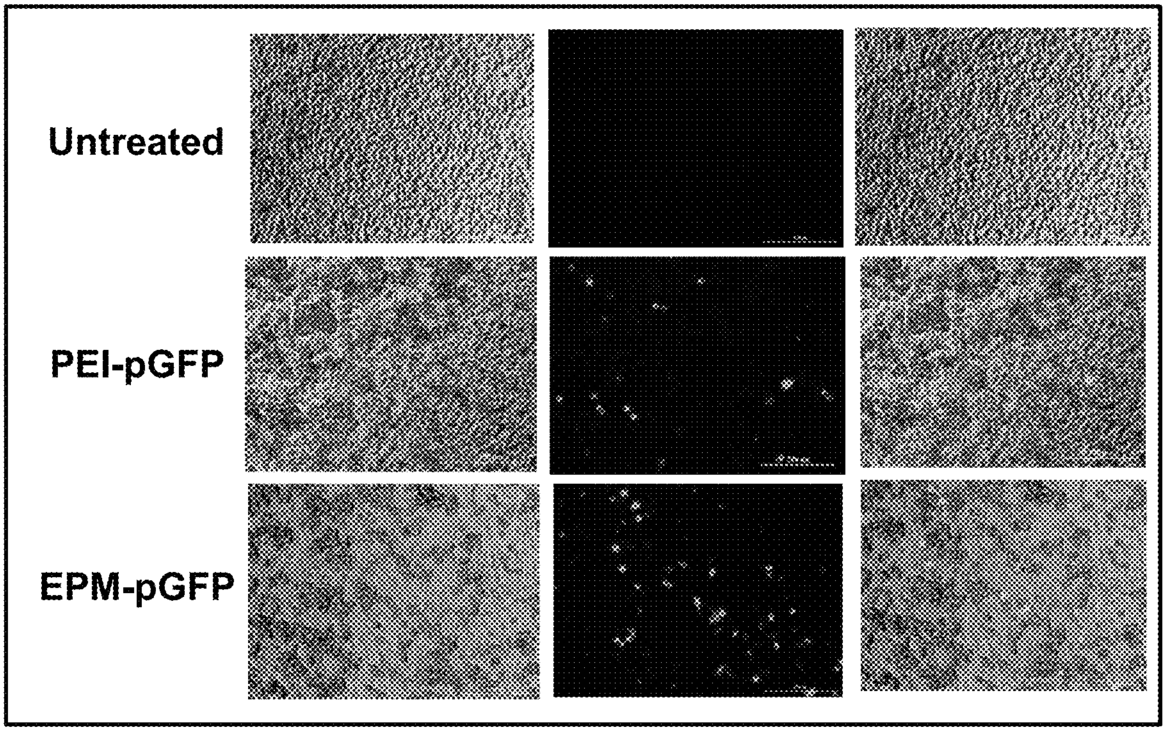
FIG. 12 is a set of micrographs of human lung cancer A549 cells treated with emerald green-fluorescent protein (eGFP) plasmid loaded on PEI and entrapped with bovine colostrum-derived exosomes complexed with PEI wherein the EPM-eGFP plasmid formulations were prepared with varying amounts of exosomes.

Transfection of human cancer cells with plasmid DNA entrapped with EPM: It has been found that the siRNA may be replaced with plasmid DNA by following the procedure used for siRNA-loaded EPM but replacing the siRNA with 0.1 μg-10 μg plasmid DNA (peGFP, p53). In studies conducted by the inventors, human lung cancer A549 cells were treated with the EPM-pP53 and microscopic studies were performed at 24 h-48 h, while functional assay by western blot analysis were performed at 24 h-72 h of treatment. Cell toxicity was measured by MTT assay after 72 hours. Lipofectamine® 2000 was used as positive control. As shown in FIG. 12, when human lung cancer A549 cells are treated with the EPM entrapped with peGFP and cells are visualized under a fluorescent microscope, the cells show high transfection with GFP with essentially no toxicity. However, the transfection is modest when cells are treated with PEI+GFP, and this formulation is accompanied with significant toxicity based on cell death. Further studies by the inventors evaluating the transfection of A549 lung cancer cells with different concentrations of eGFP plasmid DNA embedded in the PEI alone and in the EPM found that GFP protein expression levels is 8-9-fold higher when peGFP is delivered via the EPM compared with PEI alone. These data suggest that cell uptake of EPM-peGFP is much higher than the PEI-peGFP and establish superiority of the EPM system. Furthermore, increasing the pGFP amount from about 4 μg to about 7 ug or to about 10 μg does not result any higher expression of eGFP.

Figure 13:
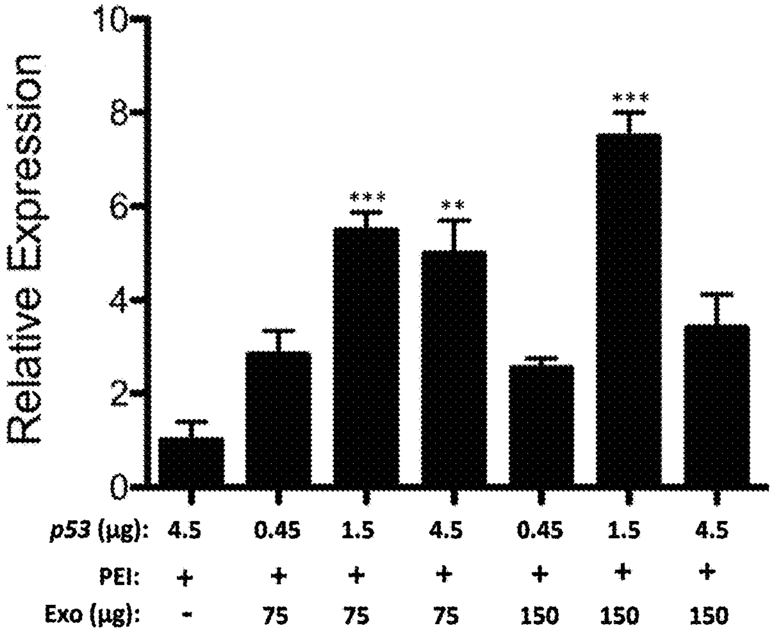
FIG. 13 is a graph showing the effect of concentration of exosomes and pP53 on the transfection of H1299 lung cancer cells with p53 plasmid DNA entrapped with the EPM, wherein p53-null H1299 lung cancer cells were transfected with EPM-pP53 and PEI-pP53 containing indicated amounts of exosomes and pP53 for 48 h, and whole cell lysates were analyzed for p53 protein levels by western blot and wherein PEI-p53 DNA is included for comparison.

Transfection efficiency varies with the amount of exosomes used (5 μg-300 μg) in preparing the EPM while maintaining PEI concentration and eGFP plasmid concentration. In studies conducted using human lung cancer H1299 cells treated with the EPM-p53 plasmid for about 48 hours, as shown in FIG. 13, it has been found that p53 expression levels increased with increasing amounts of pP53 from 0.15 μg-1.5 μg. It was further observed that 75 μg exosomes resulted in higher expression levels of p53 than did 150 μg exosomes when embedded with 1.5 μg DNA, however, the reverse was the case when the DNA amount was increased to 4.5 μg. It was also observed that EPM-p53 plasmid resulted a significantly higher (3-fold) transfection efficiency when compared with PEI-p53 plasmid. These data suggest that both the amounts of exosomes and p53 plasmid DNA are important for optimal transfection, and that EPM is a more efficient transfection vector than PEI alone. As with the EPM-siKRAS, p53 expression levels increased time-dependently as much as about 30-fold compared to control.

Transfection of human cancer cells with plasmid DNA loaded onto EPM using bovine milk exosomes: It has been found that the colostrum powder-derived exosomes may be replaced with exosomes isolated from bovine raw milk. When EPM is prepared by incubating 75 μg exosomes isolated from the milk with 0.025% PEI, followed by incubation with 2 μg of plasmid DNA (peGFP) and human H1299 lung cancer cells are transfected, cells show high transfection with no toxicity. The degree of transfection is in the same range as obtained by using EPM prepared using the colostrum powder-derived exosomes.

Transfection of human cancer cells with GFP mRNA loaded onto EPM: The siRNA may also be replaced by mRNA, such as mGFP. Human lung cancer H1299 cells treated with the EPM-GFP-mRNA formulation shows transfection of the cells as detected by the presence of GFP fluorescence in the cells by fluorescence microscopy. The highest transfection is found with the highest amount of PEI used, and the transfection efficiency of GFP-mRNA achieved by the EPM is much higher than observed with the PEI alone without the toxicity observed when PEI is used alone.

Figure 14:
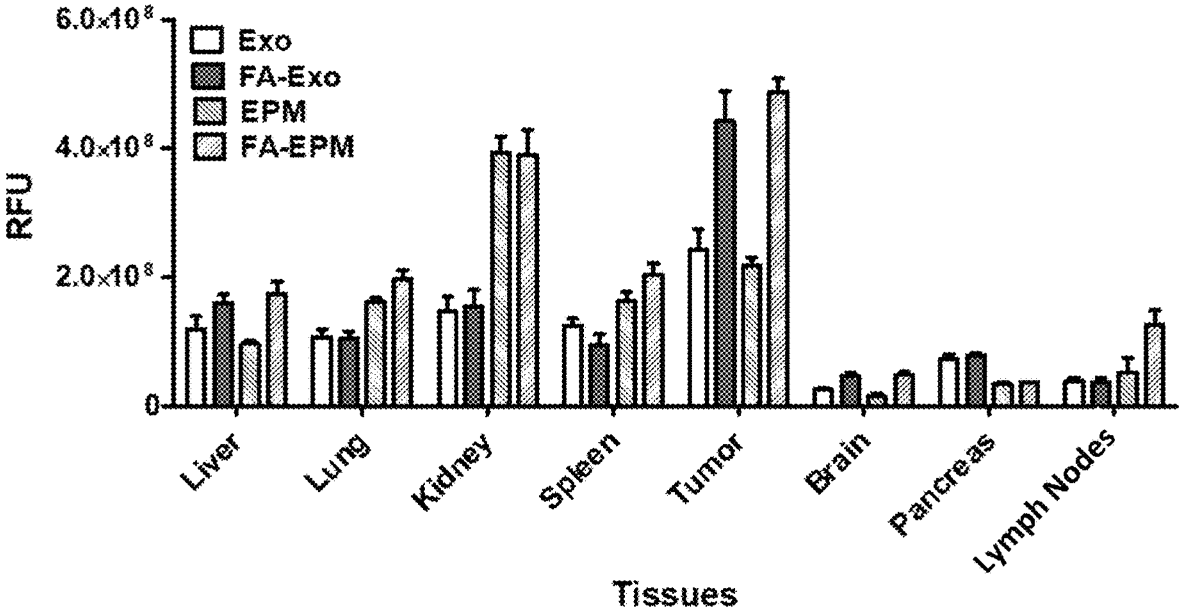
FIG. 14 is a bar graph showing the effect on A549 lung tumor tissue in nude mice of folic acid-functionalized colostrum exosomes, labeled "FA-Exo", and folic acid-functionalized EPM reagent, labeled "FA-EPM", compared to non-functionalized moieties, labeled "Exo" and "EPM", respectively, wherein the animals were euthanized 4 h after the treatment and various organs along with the tumor tissue were imaged ex vivo and wherein the controls included were untreated animals.
Figure 15:
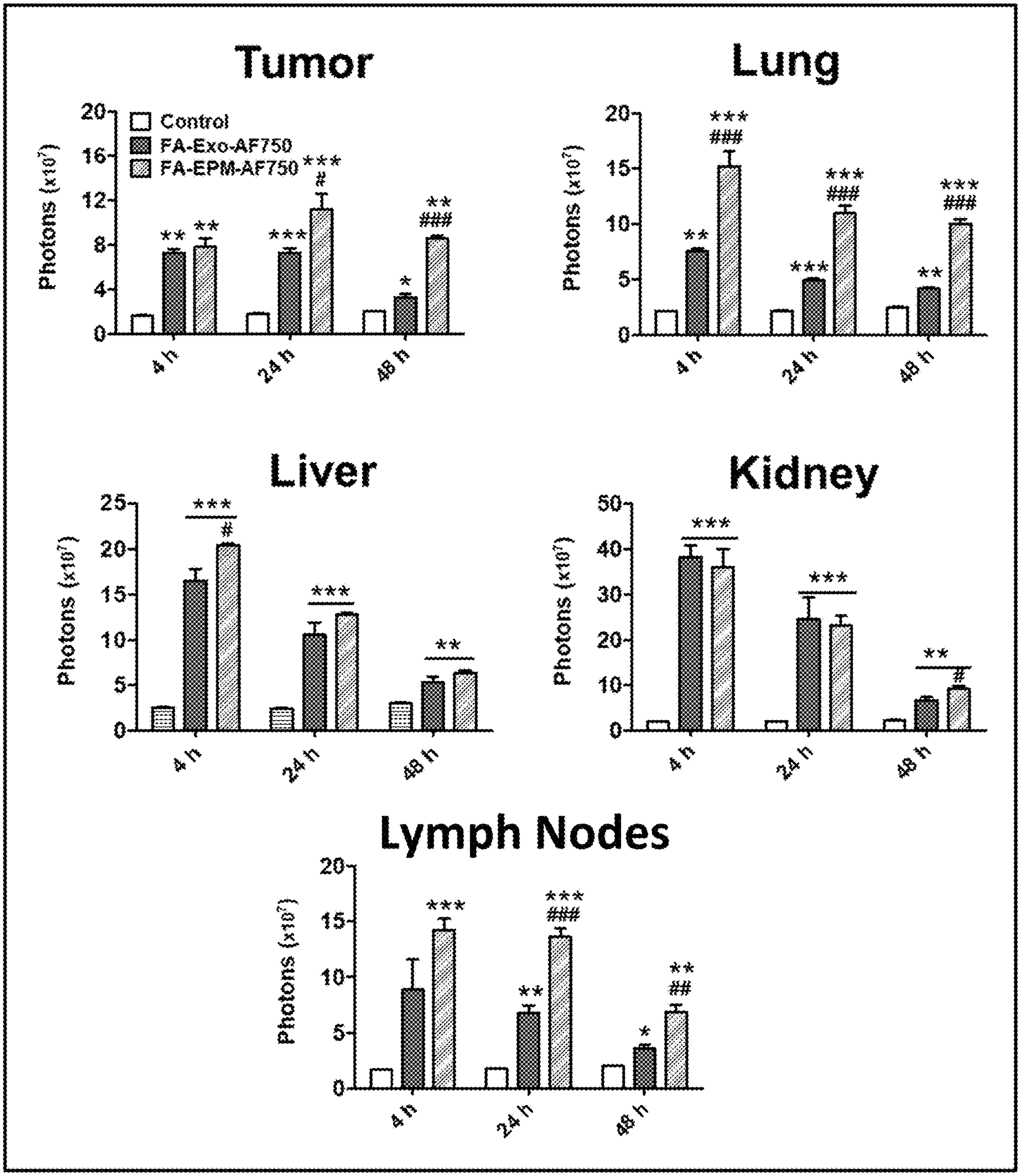
FIG. 15 is a set of bar graphs showing the biodistribution and tumor targeting of FA-Exo and FA-EPM using exosomes labeled with near infrared fluorescent dye Alexa Fluor®-750 (AF750) in the tumor, lung, liver, kidney, and lymph nodes, wherein the animals were euthanized after 4, 24 and 48 h and indicated organs and the tumor tissue were imaged ex vivo and the fluorescent intensity quantified, and wherein controls included were untreated animals; and, FIG. 16 is a graph showing the effect of siRNA of mutated KRAS (siKRAS) embedded in bovine milk-derived exosomes by the chemical transfecting reagent Exo-Fect™ on the growth of human lung cancer A549 subcutaneous tumor xenograft in female nude mice.

Tissue distribution of EPM using subcutaneous lung tumor-bearing mice: To determine tissue distribution of bovine colostrum powder-derived exosomes, with and without complexation with PEI, various formulations were tested in two tumor-bearing mouse models. To visualize exosomes in the tissue, a highly fluorescent dye Alexa Fluor®-750 (AF750) was covalently attached to the exosomes. Thus, the formulations tested included Exo-AF750, and Exo-AF750-PEI. These formulations were also functionalized with folic acid (FA) by covalently attaching FA based on carbodiimide chemistry prior to attaching AF750, thus producing FA-Exo-AF750 and FA-Exo-AF750-PEI. PEI was complexed with the Exo-AF750 and FA-Exo-AF750 using conditions previously described. It was observed that the exosome uptake by tumors followed the orders FA-Exo-AF750>Exo-AF750>AF750>untreated control and FA-Exo-AF750-PEI>Exo-AF750>untreated control, for samples without and with PEI, respectively. Interestingly, it was observed that the accumulation of FA-Exo-AF750-PEI relative to the non-FA functionalized formulation was higher than the respective non-PEI complexed formulations. Preliminary studies also indicate that the presence of PEI seems to accelerate crossing the blood-brain-barrier more easily to allow the exosomes to reach brain. As shown in FIG. 14, data from ex vivo imaging of the tumor tissues showed that FA-functionalized Exo as well as FA-functionalized EPM formulations accumulated significantly more in tumor cells compared with the non-functionalized formulations indicating the tumor-target phenomenon. Higher levels of FA-functionalized EPM were also found in lymph nodes, a novel finding, as well as in liver and brain. The biodistribution and tumor targeting of the FA-Exo and FA-EPM are shown in FIG. 15. Data show that both FA-Exo and FA-EPM formulations were delivered to all tissues examined, however, the tissue levels declined with time. The levels of both FA-Exo and FA-EPM declined significantly and continuously in the kidney and the liver. However, the reduction was modest in the lung. Interestingly, the levels of FA-EPM remained essentially constant in tumor during the 48 hours of the treatment. These data suggest that not only FA-EPM accumulate in the target tissue, i.e. tumor, the FA-EPM remain constant during 48 hours of the study. Thus, it is believed that colostrum powdered-derived exosomes following FA-functionalization can deliver the payload of siRNA to the target site and exhibit the disease inhibition.

To determine if the exosomes-PEI complex can be delivered orally, FA-Exo-AF750-PEI following purification by precipitation with ExoQuick® or by PEG-400 was given orally and intravenously to A549 lung tumor-bearing animals. The ExoQuick®-precipitated FA-Exo-AF750-PEI remained mainly in the stomach given orally, but the PEG-400-precipitated FA-Exo-AF750-PEI, which peggylate the particles and enhance GI absorption, given orally, mobilized beyond the stomach reaching not only the small intestine and colon tissues but this was also detected in the lung and kidney indicating orally delivered FA-Exo-AF750-PEI became systemic.

Figure 16:
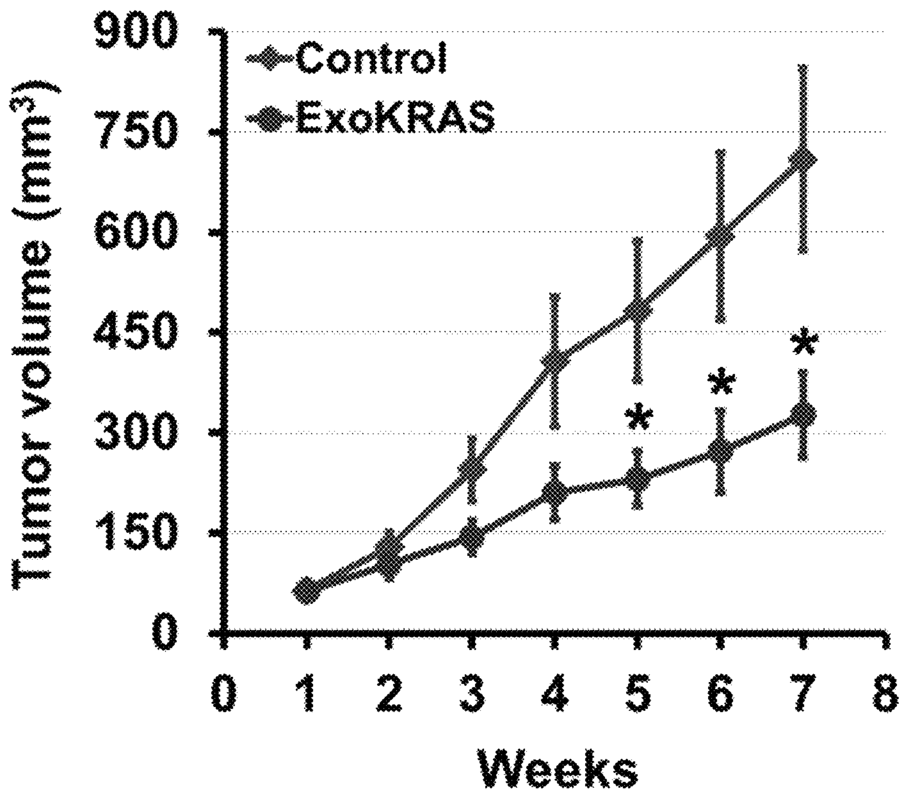

Anti-tumor efficacy of siKRAS loaded in exosomes by the Exo-Fect™ reagent: Nucleic acids also may be embedded in exosomes using Exo-Fect™ without the use of a polycation. The inventors studied female nude mice inoculated with lung cancer A549 cells with 80-100 $mm^3$ tumors and treated the mice with two intravenous doses of siKRAS embedded in bovine colostrum powder-derived exosomes by the chemical transfecting reagent Exo-Fect™, or Exo-siKRAS, with a loading to deliver about 7 μg siKRAS per dose, on a weekly basis for up to 7 weeks. It was observed that tumor size was inhibited starting at 2-3 weeks of the treatment, and the tumor inhibition became statistically significant after 5 weeks. As shown in FIG. 16, at the end of the study, the tumor growth was found to be significantly inhibited by about 55% compared to untreated controls.

Unless defined otherwise, all technical and scientific terms used herein have the same meaning as commonly understood by one of ordinary skill in the art to which the presently disclosed subject matter pertains. Representative methods, devices, and materials are described herein, but are not intended to be limiting unless so noted.

As used herein, the term “embedded” or grammatical variations thereof, when referring to biological materials, means to set or attach the biological material firmly into the receiving material or substrate while leaving some portion of the biological material exposed to the environment. As used herein, the term "entrapment" or grammatical variations thereof, when referring to biological materials, means to hold or attach the biological material onto an exterior surface of the receiving material or substrate while leaving some portion of the biological material exposed to the environment. As used herein, the term "encapsulated" or grammatical variations thereof, when referring to biological materials, means to set or attach the biological material firmly into the receiving material or substrate such that the receiving material completely surrounds the biological material preventing exposure to the environment.

As used herein, the term "complexation" means a process by which two or more materials are firmly connected by ionic interactions. As used herein, the term "complexed" means that two or more materials are combined by complexation. As used herein, a "complex" is a chemical compound formed by complexation.

The terms "a", "an", and "the" refer to "one or more" when used in the subject specification, including the claims. The term "ambient temperature" as used herein refers to an environmental temperature of from about 0° F. to about 120° F., inclusive.

Unless otherwise indicated, all numbers expressing quantities of components, conditions, and otherwise used in the specification and claims are to be understood as being modified in all instances by the term "about". Accordingly, unless indicated to the contrary, the numerical parameters set forth in the instant specification and attached claims are approximations that can vary depending upon the desired properties sought to be obtained by the presently disclosed subject matter.

As used herein, the term "about", when referring to a value or to an amount of mass, weight, time, volume, concentration, or percentage can encompass variations of, in some embodiments ±20%, in some embodiments ±10%, in some embodiments ±5%, in some embodiments ±1%, in some embodiments ±0.5%, and in some embodiments to ±0.1%, from the specified amount, as such variations are appropriate in the disclosed application.

All compositional percentages used herein are presented on a "by weight" basis, unless designated otherwise.

What is claimed is:

1. A composition for a transfection reagent comprising an exosome-polycation matrix embedded within a nucleic acid, wherein the exosome-polycation matrix comprises an isolated exosome embedded within a polycation, and wherein embedded means to set or attach the biological material firmly into the receiving material or substrate while leaving some portion of the biological material exposed to the environment.

2. The composition of claim 1 wherein the isolated exosome is derived from a milk source or a colostrum source or raw milk or raw colostrum.

3. The composition of claim 1 wherein the polycation is selected from the group consisting of polyethylenimine, polyethylenimine conjugates, polycationic peptides, polylysine, polyornithine, polyhistidine, polyarginine, DEAE-dextran, chitosan, polyamine dendrimers, and combinations thereof.

4. The composition of claim 3 wherein the polycation is a polyethylenimine.

5. The composition of claim 4 wherein the polyethylenimine polycation is selected from the group consisting of PEI-60K, PEI branched chain MW 800, PEI linear chain MW 2,500, PEI-g-polyethylene glycol (PEI-PEG), and combinations thereof.

6. The composition of claim 5 wherein the polyethylenimine polycation has a molecular weight of at least 5,000.

7. The composition of claim 1 wherein the nucleic acid is selected from the group consisting of an siRNA, a plasmid DNA, a plasmid DNA expression construct, siEGFR, siKRAS, siAKT, siMAPK, siVEGF, eGFP plasmid DNA, p53 plasmid DNA, mRNA, an antisense oligo, an aptamer, and combinations thereof.

8. The composition of claim 1 further including a fluorescent dye.

9. The composition of claim 1 further comprising a pharmaceutically-acceptable vehicle, carrier, or excipient.

10. A composition effective for transfecting target cells with a nucleic acid to knockdown target gene expression, to introduce gene expression, to enhance gene expression, or to increase immune recognition of disease cells wherein the composition comprises an exosome-polycation matrix embedded with a nucleic acid prepared by embedding an isolated exosome within a polycation to form the exosome polycation matrix and then incubating the exosome polycation matrix with the nucleic acid, wherein the nucleic acid is selected from an siRNA or a plasmid DNA or a plasmid DNA expression construct or a combination thereof, and wherein embedded means to set or attach the biological material firmly into the receiving material or substrate while leaving some portion of the biological material exposed to the environment.

11. The composition of claim 10 wherein the isolated exosome is derived from a milk source or a colostrum source or raw milk or raw colostrum.

12. The composition of claim 10 wherein the polycation is selected from the group consisting of polyethylenimine, polyethylenimine conjugates, polycationic peptides, polylysine, polyornithine, polyhistidine, polyarginine, DEAE-dextran, chitosan, polyamine dendrimers, and combinations thereof.

13. The composition of claim 12 wherein the polycation is a polyethylenimine.

14. The composition of claim 10 wherein the nucleic acid is selected from the group consisting of an siRNA, a plasmid DNA, a plasmid DNA expression construct, siEGFR, siKRAS, siAKT, siMAPK, siVEGF, eGFP plasmid DNA, p53 plasmid DNA, mRNA, an antisense oligo, an aptamer, and combinations thereof.

* * * * *